United States Patent
Unni et al.

(10) Patent No.: US 11,724,971 B2
(45) Date of Patent: Aug. 15, 2023

(54) PROCESS FOR MAKING [1.1.1]PROPELLANE

(71) Applicant: Recurium IP Holdings, LLC, San Diego, CA (US)

(72) Inventors: Aditya Krishnan Unni, San Diego, CA (US); Joseph Robert Pinchman, San Diego, CA (US); Peter Qinhua Huang, San Diego, CA (US); Kevin Duane Bunker, Escondido, CA (US)

(73) Assignee: Recurium IP Holdings, LLC, San Diego, CA (US)

( * ) Notice: Subject to any disclaimer, the term of this patent is extended or adjusted under 35 U.S.C. 154(b) by 0 days.

(21) Appl. No.: 17/634,879

(22) PCT Filed: Aug. 12, 2020

(86) PCT No.: PCT/US2020/045869
§ 371 (c)(1),
(2) Date: Feb. 11, 2022

(87) PCT Pub. No.: WO2021/030401
PCT Pub. Date: Feb. 18, 2021

(65) Prior Publication Data
US 2022/0324775 A1 Oct. 13, 2022

Related U.S. Application Data

(60) Provisional application No. 62/886,769, filed on Aug. 14, 2019.

(51) Int. Cl.
*C07C 1/28* (2006.01)
*C07C 13/605* (2006.01)

(52) U.S. Cl.
CPC ............. *C07C 1/28* (2013.01); *C07C 13/605* (2013.01); *C07C 2521/10* (2013.01)

(58) Field of Classification Search
CPC ...................................................... C07C 1/28
See application file for complete search history.

(56) References Cited

FOREIGN PATENT DOCUMENTS

WO  WO-2017157932 A1 * 9/2017 ............... C07C 1/28
WO  WO 2019/051038 A1  3/2019

OTHER PUBLICATIONS

Belzner, Johannes, et al. "Concerning the synthesis of [1.1.1]propellane." Chemische Berichte 122, (1989), 397-398, https://doi.org/10.1002/cber.19891220233.
D'Yachenko, A.I., Abramova, N.M., Zotova, S.V. et al. New synthesis of bicyclo[1.1.0]butane hydrocarbons. Russ Chem Bull 34, 1885-1889 (1985), https://doi.org/10.1007/BF00953929.
Lampman, Gary, et al. "Bicyclo[1.1.0]Butane", Organic Syntheses, Coll. vol. 6, p. 133 (1988); vol. 51, p. 55 (1971), DOI:10.15227/orgsyn.051.0055.
Mondanaro Lynch, K. and Dalley, W.P. (2003). [1.1.1]Propellane. In Organic Syntheses, (Ed.), DOI: 10.1002/0471264180.os075.12.
Semmler, Klaus, Guenter Szeimies, and Johannes Belzner. "Tetracyclo[5.1.0.01,6.02,7]octane, a [1.1.1]propellane derivative, and a new route to the parent hydrocarbon." Journal of the American Chemical Society 107, (1985), 6410-6411, https://doi.org/10.1021/ja00308a053.
Shelp, Russell A., and Patrick J. Walsh. "Synthesis of BCP benzylamines from 2-azaallyl anions and [1.1.1]propellane." Angewandte Chemie International Edition 57, (2018), 15857-15861, https://doi.org/10.1002/anie.201810061.
Shtarev, Alexander B., et al. "Partially Bridge-Fluorinated Dimethyl Bicyclo[1.1.1]pentane-1,3-dicarboxylates: Preparation and NMR Spectra." Journal of the American Chemical Society 123, (2001), 3484-3492, https://doi.org/10.1021/ja0000495.

* cited by examiner

*Primary Examiner* — Philip Y Louie
*Assistant Examiner* — Alyssa L Cepluch
(74) *Attorney, Agent, or Firm* — Knobbe, Martens, Olson & Bear, LLP

(57) ABSTRACT

Processes of making [1.1.1]propellane utilize reaction conditions that include reacting 1,1-dibromo-2,2-bis(chloromethyl)cyclopropane with an effective amount of solid magnesium.

21 Claims, No Drawings

PROCESS FOR MAKING [1.1.1]PROPELLANE

INCORPORATION BY REFERENCE TO ANY PRIORITY APPLICATIONS

This application claims priority to U.S. Ser. No. 62/886,769, filed Aug. 14, 2019, which is hereby incorporated herein by reference in its entirety.

BACKGROUND

Field

This application relates to processes for making bicyclic compounds, and particularly for making [1.1.1]propellane under reaction conditions that include reacting 1,1-dibromo-2,2-bis(chloromethyl)cyclopropane with magnesium.

Description

The traditional process for making tricyclo[1.1.1.0$^{1,3}$]pentane (also known as [1.1.1]propellane) is a batch reaction of 1,1-dibromo-2,2-bis(chloromethyl)cyclopropane with methyllithium (MeLi) under rigorously anhydrous reaction conditions as follows:

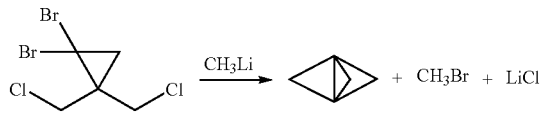

See K. R. Mondanaro and W. P. Dailey, Org. Synth. 75 (1998) p. 98. The process as described by Mondanaro et al. results in the formation of 2 equivalents of methyl bromide (MeBr) as a side product. The MeBr does not react with [1.1.1]propellane but it is difficult to remove and can cause significant problems when running downstream reactions using anionic chemistries such as organo alkali or organo magnesium reactions. While there is an alternative preparation of [1.1.1]propellane that utilizes phenyllithium (PhLi) in place of MeLi, the quality of the PhLi can significantly impact yields, and the corresponding 2 equivalents of produced phenyl bromide (PhBr) can interfere with downstream reactions. The produced PhBr can be removed by co-distillation of [1.1.1]propellane solutions with a low boiling carrier solvent but the process is burdensome on commercial scales. In addition, such traditional batch procedures generally require careful reaction temperature control (e.g., −78° C. to −40° C.), particularly during the initial stages of the reaction, which on production/kilogram scale would lead to increased costs and scalability issues.

The use of a lithium dispersion in place of MeLi has also been reported:

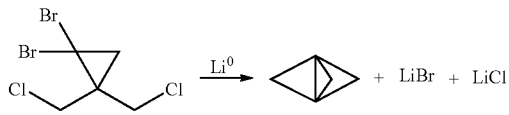

See J. Belzner et al., Chem. Ber. 122 (1989) 397-398. However, due to the potentially violent reactivity of alkali metals with air and moisture, reactions involving elemental lithium are challenging to handle, particularly on a large scale.

The use of solid magnesium has been reported for the cyclization of 1-bromo-2-(chloromethyl)cyclopropane to form bicyclo[1.1.0]butane (BCB). However, considerable amounts of unsaturated hydrocarbon side products were obtained, as well as undesirable yields and a complicated isolation of BCB. See A. I. D'yachenko, Izvestiya Akademii Nauk SSSR, Seriya Khimicheskaya, No. 9, (1985) 2043-2047. Accordingly, improved processes for making [1.1.1]propellane are desired.

SUMMARY

A process has now been developed for making [1.1.1]propellane under substantially anhydrous reaction conditions that include reacting 1,1-dibromo-2,2-bis(chloromethyl)cyclopropane with an effective amount of elemental magnesium in accordance with Scheme (I) as follows:

Scheme (I)

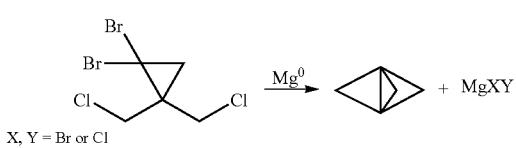

X, Y = Br or Cl

Surprisingly, even though elemental magnesium is generally considered much less reactive with alkyl halides than MeLi, PhLi and/or elemental lithium, relatively mild reaction conditions have been identified that enable commercially acceptable productivity and yields of [1.1.1]propellane.

An embodiment provides a process of making [1.1.1]propellane, comprising reacting 1,1-dibromo-2,2-bis(chloromethyl)cyclopropane with an effective amount of solid magnesium under substantially anhydrous reaction conditions that are selected to produce [1.1.1]propellane.

These and other embodiments are described in greater detail below.

DETAILED DESCRIPTION

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. A group of items linked with the conjunction 'and' should not be read as requiring that each and every one of those items be present in the grouping, but rather should be read as 'and/or' unless the context indicates otherwise (e.g., in the claims). A group of items linked with the conjunction 'or' should not be read as requiring mutual exclusivity among that group, but rather should be read as 'and/or' unless the context indicates otherwise. Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

As used herein, the term "substantially anhydrous" has its usual meaning as understood by those skilled in the art in the context of describing conditions suitable for reacting 1,1-dibromo-2,2-bis(chloromethyl)cyclopropane with an effective amount of solid magnesium, and thus includes reaction conditions in which the amount of water and/or oxygen are minimized to reduce undesired side reactions. Such substantially anhydrous reaction conditions are generally similar to the well-understood conditions used for Grignard reactions.

As used herein, the term "continuous flow process" and similar terms are used to refer to a chemical process that utilizes flow chemistry and technology. Examples of such processes are disclosed in WO 2019/051038, published 14 Mar. 2019, which is hereby incorporated herein by reference and particularly for the purpose of describing continuous flow process techniques, equipment and reaction conditions.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Processes of Making [1.1.1]Propellane

Various embodiments provide a process of making [1.1.1]propellane, comprising reacting 1,1-dibromo-2,2-bis(chloromethyl)cyclopropane with an effective amount of solid magnesium under substantially anhydrous reaction conditions that are selected to produce [1.1.1]propellane. The relative amounts of 1,1-dibromo-2,2-bis(chloromethyl)cyclopropane and solid magnesium may be selected to achieve a desired yield in accordance with the reaction stoichiometry. For example, in an embodiment, the effective amount of the solid magnesium is a molar excess that is at least 2× with respect to 1,1-dibromo-2,2-bis(chloromethyl)cyclopropane, e.g., at least 2.1× or 2.2×. The solid magnesium may be in various forms, such as commercially available magnesium turnings that have an advantageously high surface area for the heterogeneous reaction with the 1,1-dibromo-2,2-bis(chloromethyl)cyclopropane.

In contrast to the rigorously anhydrous reaction conditions used when employing MeLi and elemental lithium reagents as described above, embodiments of the substantially anhydrous reaction conditions described herein utilize solid elemental magnesium, which is generally less sensitive to water and/or oxygen than lithium. In various embodiments this reduced sensitivity enhances safety without compromising productivity, thus facilitating fruitful scale up and commercial viability. For example, in an embodiment, a process of making [1.1.1]propellane comprises contacting at least about one kilogram of 1,1-dibromo-2,2-bis(chloromethyl)cyclopropane with the effective amount of solid magnesium under substantially anhydrous reaction conditions as described herein.

In various embodiments, the substantially anhydrous reaction conditions comprise reacting 1,1-dibromo-2,2-bis(chloromethyl)cyclopropane with the solid magnesium in the presence of an aprotic ether solvent. In an embodiment, the aprotic ether solvent comprises tetrahydrofuran (THF). In various embodiments, the aprotic ether solvent comprises THF and further comprises an ether selected from diethylether, diethoxymethane, dibutylether, methyl tert-butyl ether, dioxane, 2-methyltetrahydrofuran, cyclopentyl methyl ether, and mixtures thereof. In other embodiments, the aprotic ether solvent further comprises a hydrocarbon solvent for the 1,1-dibromo-2,2-bis(chloromethyl)cyclopropane and the [1.1.1]propellane. In an embodiment, the hydrocarbon solvent is toluene, heptane or a mixture thereof. The amount of hydrocarbon solvent in admixture with the aprotic ether solvent can be selected to result in at least partial insolubility for the resulting produced salts (e.g., $MgBrCl$, $MgBr_2$ and/or $MgCl_2$), thus facilitating workup of the produced [1.1.1]propellane reaction mixture by at least partially removing the produced insoluble salt(s) by a suitable separation technique (e.g., filtration) to result in a purified [1.1.1]propellane or partially purified mixture thereof.

Surprisingly, it has been found that the amount of THF in a solvent mixture can affect the yield of produced [1.1.1]

propellane under the substantially anhydrous reaction conditions described herein. In an embodiment, the aprotic ether solvent comprises an amount of THF that is effective to enhance the yield of produced [1.1.1]propellane, in comparison to an otherwise comparable solvent that lacks such an amount of THF.

The substantially anhydrous reaction conditions may comprise a relatively wide range of reaction temperatures. As noted above, traditional batch reaction conditions for producing [1.1.1]propellane typically require low initial temperatures ranging from −78° C. to −40° C., with gradual warming to temperatures greater than −40° C. being conducted carefully at later stages, towards the end of the reaction. It has now been found that when the [1.1.1] propellane is produced using an effective amount of magnesium as described herein, the initial stage of the reaction can be conducted at significantly higher temperatures, such as at about −20° C. or higher. For example, in various embodiments, such significantly higher temperatures for the substantially anhydrous reaction conditions can comprise a reaction temperature that is much more amenable to commercial production, such as a temperature in the range of from about 0° C. up to the reflux temperature of the reaction mixture. In an embodiment, the substantially anhydrous reaction conditions comprise a reaction temperature in the range of about 0° C. to about 85° C. The reaction temperature can be selected using routine experimentation guided by the teachings provided herein. Control of the reaction temperature can be accomplished in various ways known to those skilled in the art, such as by applying external heating or cooling, controlling the relative feed rates of the 1,1-dibromo-2,2-bis(chloromethyl)cyclopropane and solid magnesium reagents, and/or controlling reaction pressure (and thus, for example, the reflux temperature).

The substantially anhydrous reaction conditions may comprise a relatively wide range of reaction pressures. For example, in various embodiments, the substantially anhydrous reaction conditions comprise a reaction pressure in the range of about 10 kPa to about 500 kPa. The reaction pressure can be selected using routine experimentation guided by the teachings provided herein. Control of the reaction pressure can be accomplished in various ways known to those skilled in the art, such as by conducting the reaction in a pressurized vessel (e.g., by fitting the reaction vessel with a balloon) and/or by applying an external vacuum. Pressures in the range of slightly above ambient (e.g., about 102 kPa) to about 1000 kPa are useful for increasing the boiling point of the produced [1.1.1]propellane, thereby reducing volatility and/or increasing yield.

The substantially anhydrous reaction conditions may comprise a relatively wide range of reaction times for the 1,1-dibromo-2,2-bis(chloromethyl)cyclopropane and solid magnesium reactants. For example, in various embodiments, the substantially anhydrous reaction conditions comprise a reaction time in the range of about 30 minutes to about 10 hours. In some embodiments, such as when the reaction conditions comprise continuous flow conditions as described elsewhere herein, the reaction time can be shorter. For example, in various embodiments, the substantially anhydrous reaction conditions comprise a reaction time in the range of about 30 seconds to about 30 minutes. The reaction time can be selected using routine experimentation guided by the teachings provided herein. Surprisingly, relatively high yields of [1.1.1]propellane can be obtained at convenient reaction temperatures and short reaction times by the practice of embodiments as described herein, e.g., as illustrated in Examples 1-3 below. In practice, reaction times are typically selected in combination with reaction temperatures and/or the relative feed rates of the 1,1-dibromo-2,2-bis(chloromethyl)cyclopropane and solid magnesium reactants, to achieve a desired productivity of the produced [1.1.1]propellane.

The substantially anhydrous reaction conditions may comprise a batch condition and/or a continuous flow condition. For example, batch conditions are illustrated in the examples below. Suitable continuous flow conditions can be identified by those skilled in the art, as informed by the disclosure of WO 2019/051038 using routine experimentation guided by the teachings provided herein.

Surprisingly, in spite of the generally lower expectation regarding its reactivity as compared to MeLi or solid lithium, substantially anhydrous reaction conditions that include solid magnesium have now been identified that result in relatively high yields of produced [1.1.1]propellane. In an embodiment, the substantially anhydrous reaction conditions are selected to produce a yield of the produced [1.1.1]propellane that is about 10% or higher (e.g., in the range of about 10% to about 90%). In another embodiment, the substantially anhydrous reaction conditions are selected to produce a yield of the produced [1.1.1]propellane that is about 20% or higher (e.g., in the range of about 20% to about 90%). In another embodiment, the substantially anhydrous reaction conditions are selected to produce a yield of the produced [1.1.1]propellane that is about 30% or higher (e.g., in the range of about 30% to about 90%). In another embodiment, the substantially anhydrous reaction conditions are selected to produce a yield of the produced [1.1.1] propellane that is about 40% or higher (e.g., in the range of about 40% to about 90%). In another embodiment, the substantially anhydrous reaction conditions are selected to produce a yield of the produced [1.1.1]propellane that is about 50% or higher (e.g., in the range of about 50% to about 90%). Those skilled in the art can use routine experimentation guided by the detailed teachings provided herein to identify suitable substantially anhydrous reaction conditions for obtaining desired yields. For example, in an embodiment, a desired yield (e.g., at least about 10%, 20%, 30%, 40%, or 50%) is obtained by employing a combination of any two or more of a reaction temperature, a reaction time, a reaction pressure, a THF content in the aprotic ether solvent, and/or a relative feed rate of 1,1-dibromo-2,2-bis (chloromethyl)cyclopropane and solid magnesium, as taught herein.

In various embodiments, an initial product of the reaction of the 1,1-dibromo-2,2-bis(chloromethyl)cyclopropane with the effective amount of solid magnesium is a reaction mixture that contains the produced [1.1.1]propellane, along with remaining reactant(s), solvent(s), and/or produced side products (such as salts). The produced [1.1.1]propellane can be isolated and purified from the reaction mixture in various ways. For example, a standard aqueous workup followed by extraction with an organic solvent can be used to purify the [1.1.1]propellane, and may be preferred when conducted on a laboratory scale. At larger scales, it may be preferable to remove the [1.1.1]propellane over the course of the reaction and/or after the reaction is substantially complete. For example, in an embodiment the produced [1.1.1]propellane is isolated from the reaction mixture by distillation under reduced pressure as illustrated in Examples 1-2 below. Other methods of isolation (such as filtration to remove insoluble salt as described herein) may also be used.

The product produced by purifying a reaction mixture can be used as isolated or may be further purified as desired. For example, the produced [1.1.1]propellane that is isolated from the reaction mixture by distillation under reduced pressure may be sufficiently pure for subsequent use. In an embodiment, the produced [1.1.1]propellane is purified to provide a purified [1.1.1]propellane that has a purity of about 90% or higher. In some embodiments, further purification is desired of the [1.1.1]propellane-containing product produced by an initial stage of isolation. Such purification can be carried out by methods known to those skilled in the art as guided by the teachings provided herein, such as by distillation. In an embodiment, the produced [1.1.1]propellane is purified to provide a purified [1.1.1]propellane that has a purity of about 95% or higher. In another embodiment, the produced [1.1.1]propellane is purified to provide a purified [1.1.1]propellane that has a purity of about 95% or higher. Purity can be determined by methods known to those skilled in the art, such as gas chromatography (GC).

EXAMPLES

Additional embodiments are disclosed in further detail in the following examples, which are not in any way intended to limit the scope of the claims.

Example 1

1 g of magnesium turnings was added to a dry flask under an atmosphere of nitrogen. 10 mL anhydrous THF was added to cover the turnings. A cannula was connected between the reaction flask and an empty flask kept in a dry ice/acetone bath. Substantially anhydrous reaction conditions were established by adding a solution of 1,1-dibromo-2,2-bis(chloromethyl)cyclopropane (6 g) in 20 mL THF gradually to the reaction flask while maintaining a gentle reflux with the aid of a heating bath. The resulting [1.1.1] propellane was recovered continuously by applying partial vacuum to the cold receiving flask. The collected solution of propellane in THF was weighed and analysis by $^1$H NMR indicated the yield of the [1.1.1]propellane to be 36%.

Example 2

0.58 grams of magnesium turnings was added to dry flask containing a stirbar and a thermocouple probe through a septum on the flask and then placed under an atmosphere of nitrogen. An aprotic ether solvent containing 10 mL of THF and methyl tert-butyl ether in a 1:1 volume ratio was added to the flask. The flask was then heated to 30° C. Separately, 1,1-dibromo-2,2-bis(chloromethyl)cyclopropane (3 g) was dissolved in 10 mL of THF and methyl tert-butyl ether in a 1:1 volume ratio. Substantially anhydrous reaction conditions were established by adding approximately ⅒ of this solution to the reaction flask followed by 0.48 mL of diisobutylaluminum hydride (1M in THF). After 15 min, the remainder of the solution of 1,1-dibromo-2,2-bis(chloromethyl)cyclopropane was added gradually under the anhydrous reaction conditions to keep the temperature of the reaction at about 40-50° C. After an additional 30 min, the resulting mixture of aprotic ether solvent and produced [1.1.1]propellane was transferred under a partial vacuum to a cold receiving flask. The collected solution of [1.1.1] propellane and solvents was weighed and analysis by $^1$H NMR indicated the yield of the [1.1.1]propellane to be 42%.

Example 3

0.73 grams of magnesium turnings was added to flask containing a stirbar. The flask was fitted with a rubber septum with a digital thermocouple and then placed under an atmosphere of nitrogen. 10 mL of THF and 1.0 mL of diisobutylaluminum hydride (1M in THF) was added to the flask. After 1 h, substantially anhydrous reaction conditions were established by adding a solution of dibromo-2,2-bis(chloromethyl)cyclopropane (3 g) in THF (9 mL) to the flask at a rate to maintain the reaction temperature to 20-25° C. After an additional 1 h, an aliquot of the solution was checked by $^1$H NMR and indicated the yield of propellane to be 54%.

What is claimed is:

1. A process of making [1.1.1]propellane, comprising reacting 1,1-dibromo-2,2-bis(chloromethyl)cyclopropane with an effective amount of solid magnesium under substantially anhydrous reaction conditions that are selected to produce [1.1.1]propellane.

2. The process of claim 1, wherein the substantially anhydrous reaction conditions comprise reacting 1,1-dibromo-2,2-bis(chloromethyl)cyclopropane with the solid magnesium in the presence of an aprotic ether solvent that comprises tetrahydrofuran.

3. The process of claim 2, wherein the aprotic ether solvent further comprises an ether selected from diethylether, diethoxymethane, dibutylether, methyl tert-butyl ether, dioxane, 2-methyltetrahydrofuran, cyclopentyl methyl ether, and mixtures thereof.

4. The process of claim 2, wherein the aprotic ether solvent further comprises a hydrocarbon solvent for the 1,1-dibromo-2,2-bis(chloromethyl)cyclopropane and the [1.1.1]propellane.

5. The process of claim 4, wherein the hydrocarbon solvent is selected from toluene and heptane.

6. The process of claim 4, further comprising filtering a reaction mixture resulting from the reacting to thereby at least partially remove at least one insoluble salt.

7. The process of claim 1, wherein the effective amount of the solid magnesium is a molar excess that is at least 2×with respect to 1,1-dibromo-2,2-bis(chloromethyl)cyclopropane.

8. The process of claim 1, wherein the substantially anhydrous reaction conditions are further selected to produce a yield of the produced [1.1.1]propellane that is about 10% or higher.

9. The process of claim 8, wherein the yield is about 20% or higher.

10. The process of claim 8, wherein the yield is about 30% or higher.

11. The process of claim 8, wherein the yield is about 40% or higher.

12. The process of claim 8, wherein the yield is about 50% or higher.

13. The process of claim 1, wherein the substantially anhydrous reaction conditions comprise a reaction temperature in the range of about 0° C. to about 85° C.

14. The process of claim 1, wherein the substantially anhydrous reaction conditions comprise a reaction time in the range of about 30 minutes to about 10 hours.

15. The process of claim 1, further comprising separating at least a portion of the produced [1.1.1]propellane from a reaction mixture containing the 1,1-dibromo-2,2-bis(chloromethyl)cyclopropane and the solid magnesium.

16. The process of claim 1, comprising contacting at least about one kilogram of 1,1-dibromo-2,2-bis(chloromethyl) cyclopropane with the effective amount of solid magnesium.

17. The process of claim 1, further comprising purifying the produced [1.1.1]propellane to provide a purified [1.1.1] propellane that has a purity of about 90% or higher.

18. The process of claim 17, wherein the purity is about 95% or higher.

19. The process of claim 18, wherein the purity is about 99% or higher.

20. The process of claim 1, wherein the substantially anhydrous reaction conditions comprise a batch condition.

21. The process of claim 1, wherein the substantially anhydrous reaction conditions comprise a continuous flow reaction condition conducted in a continuous flow reactor.

* * * * *